(12) United States Patent
Dolgov et al.

(10) Patent No.: US 6,646,444 B2
(45) Date of Patent: Nov. 11, 2003

(54) PLUG-IN PHOTOIONIZATION SENSOR

(75) Inventors: Boris N. Dolgov, Longmont, CO (US); Donald K. Forsberg, Johnstown, CO (US)

(73) Assignee: Mocon, Inc., Minneapolis, MN (US)

( * ) Notice: Subject to any disclaimer, the term of this patent is extended or adjusted under 35 U.S.C. 154(b) by 44 days.

(21) Appl. No.: 10/057,625

(22) Filed: Jan. 24, 2002

(65) Prior Publication Data

US 2003/0137306 A1 Jul. 24, 2003

(51) Int. Cl.⁷ .............................. G01N 27/64; G01T 1/18
(52) U.S. Cl. ........................................ 324/469; 250/382
(58) Field of Search ................................ 324/459, 469; 250/464, 382, 371, 372, 281

(56) References Cited

U.S. PATENT DOCUMENTS 5,773,833 A * 6/1998 Hsi .............................. 250/382
6,124,678 A * 9/2000 Bishop et al. ........ 315/209 PZ

* cited by examiner

*Primary Examiner*—N. Le
*Assistant Examiner*—Donald M Lair
(74) *Attorney, Agent, or Firm*—Paul L. Sjoquist

(57) ABSTRACT

A sensor for detecting volatile organic compounds in ambient air by positioning a detection cell adjacent a gas discharge device to cause molecules of organic compounds to become ionized, and applying an electric field across the collection cell to attract ions and free electrons formed in the cell to develop a current, and amplifying the current magnitude so created.

18 Claims, 4 Drawing Sheets

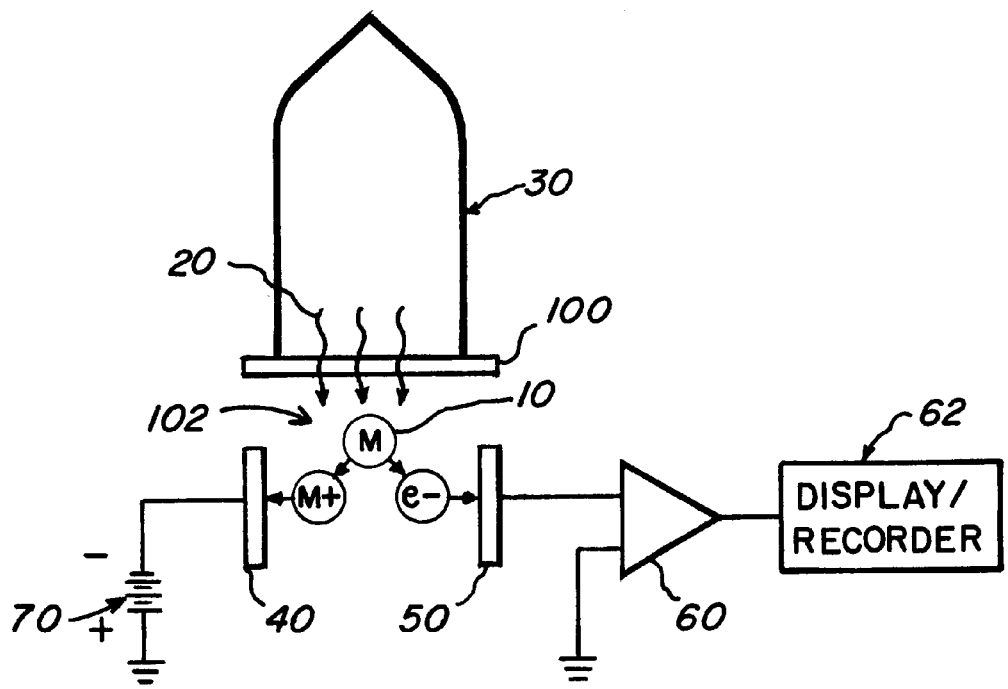
FIG. 1
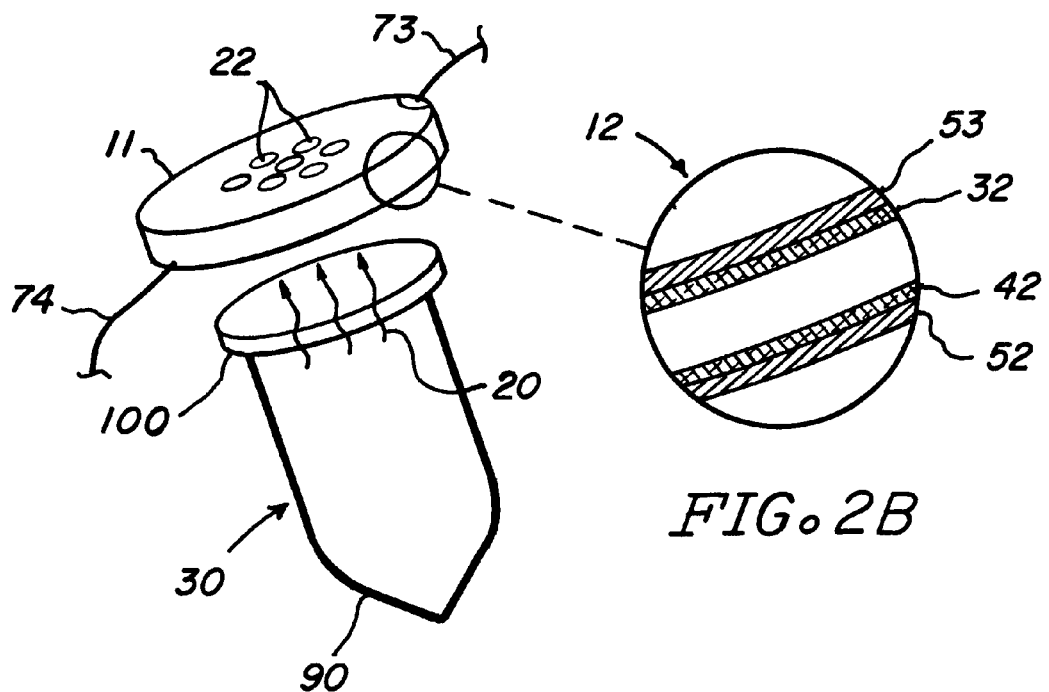
FIG. 2B
FIG. 2A

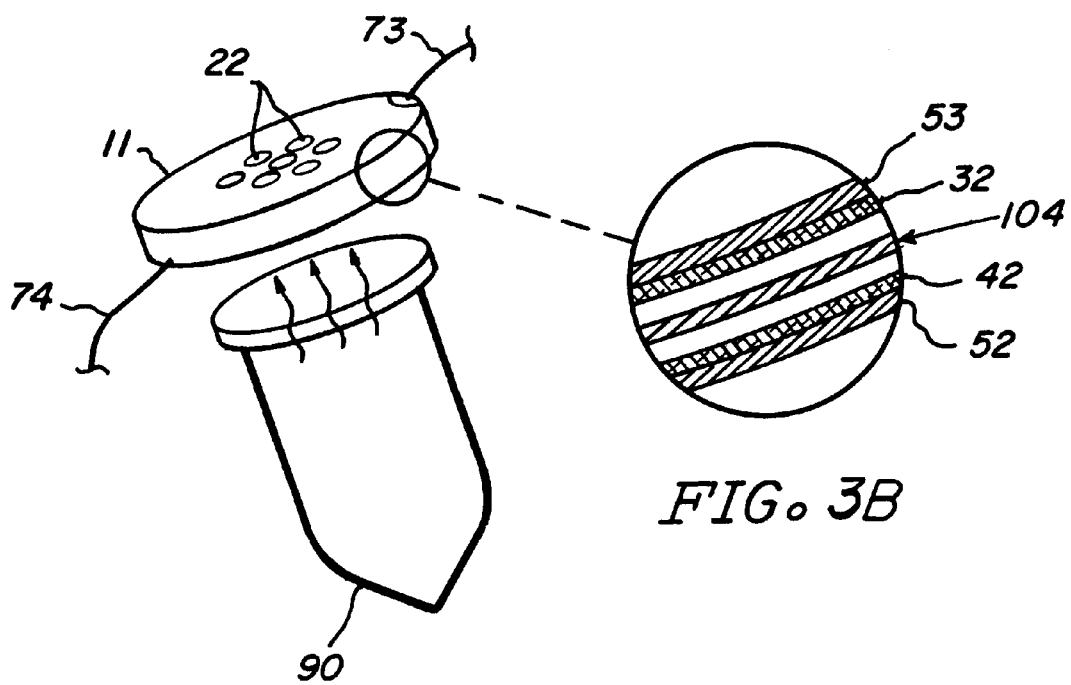
FIG. 3A
FIG. 3B
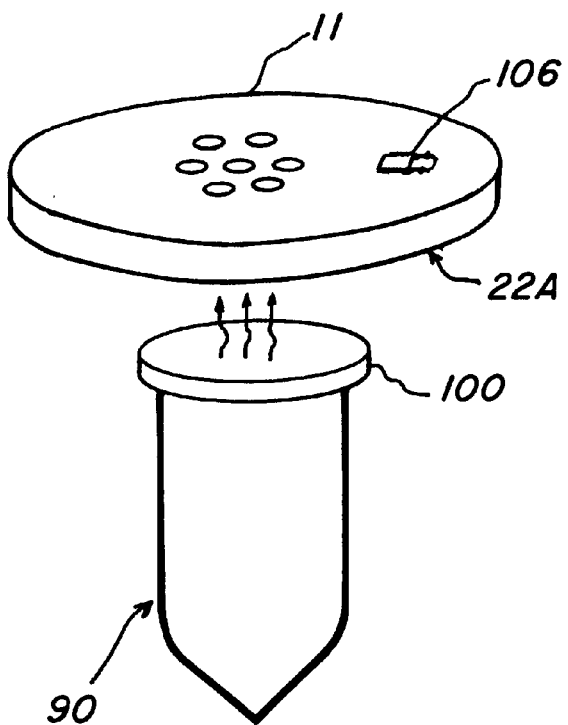
FIG. 4

PLUG-IN PHOTOIONIZATION SENSOR

BACKGROUND OF THE INVENTION

The present invention relates to an apparatus for detecting organic compounds in ambient air. More particularly, the apparatus is based on a photoionization sensor of sufficiently small size so as to be useful in portable multi-sensor instruments.

The apparatus uses a very small, high-energy, vacuum ultraviolet radiation device, which is attached to a chamber exposed to the ambient air of interest. The chamber is subjected to an electric field. The radiation device is a gas discharge lamp connected to a suitable voltage source. A certain percentage of the organic compounds in this ambient air chamber will become ionized, ie., converted into positively charged ions and negatively charged electrons. The major constituents of the ambient air, such as nitrogen ($N_2$) and oxygen ($O_2$), are unaffected by the radiation device because the energy of the radiation (8.5–11.7 eV) is too low to cause ionization of these constituents. The positive and negative ionization charges are collected by suitable electrodes, thereby generating a current which may be measured to provide an indication of the concentration of organic compounds found in the ambient air.

Therefore, the apparatus is very useful for detection of a wide range of volatile organic compounds in ambient air, in concentrations as low as in the parts-per-billion (ppb) range, without interference from air components.

SUMMARY OF THE INVENTION

An ultraviolet radiation source is constructed of a glass housing having a window at one end and being filled with an inert gas such as krypton or argon. A dielectric plate having a pattern of holes drilled proximate its center is placed adjacent the window after a thin metal layer is placed on either side of the plate, and each of the layers is covered with a thin layer of dielectric material. The gas in the lamp housing is excited by a capacitively-coupled radio frequency voltage, causing ultraviolet illumination in the pattern of holes. The apparatus is placed near a source of ambient air containing volatile organic compounds, and the ultraviolet illumination causes ionization of some of the organic compound molecules which have migrated into the pattern of holes. A DC voltage is placed across the metal layers on either side of the dielectric plate, and the charges from the ionized molecules are collected in the metal layers to cause a current to flow; the current is measured to provide a measure of the concentration of volatile organic compounds in the ambient air.

BRIEF DESCRIPTION OF THE DRAWINGS

FIG. 1 shows a simplified diagram illustrating the overall functioning of the apparatus;

FIG. 2A shows an exploded view of the gas discharge lamp and dielectric plate;

FIG. 2B shows an expanded view of a portion of the dielectric plate;

FIG. 3 shows an alternative construction of the dielectric plate;

FIG. 4 shows a miniature hybrid electronic circuit built on the dielectric plate;

DESCRIPTION OF THE PREFERRED EMBODIMENT

Figure 5:
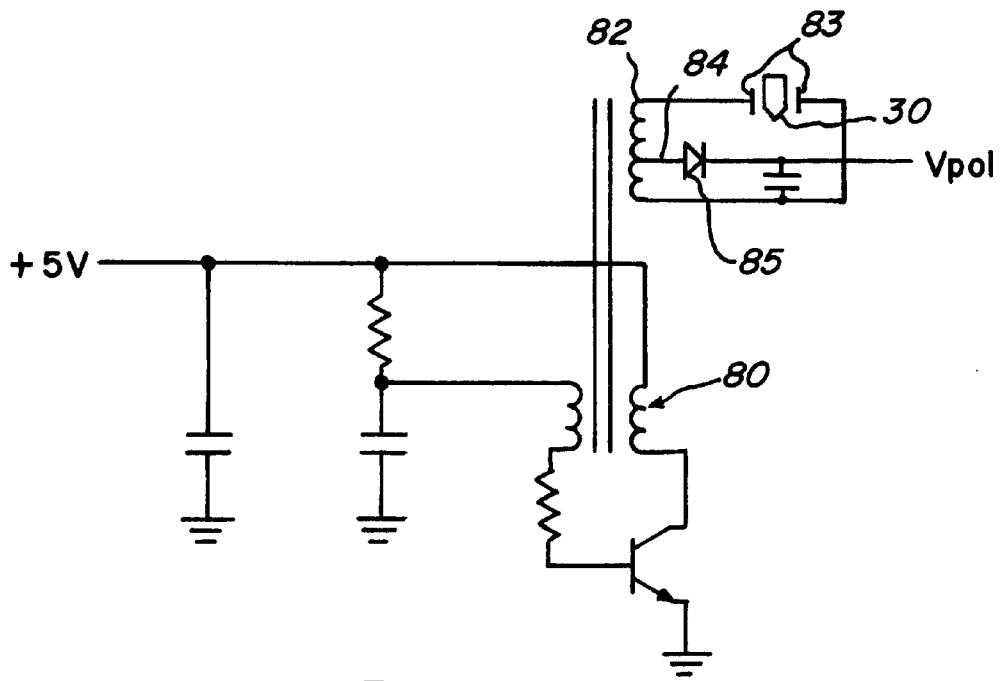
FIG. 5 shows one form of electronic circuit for energizing and driving the components of the sensor.

Referring first to FIG. 1, a simplified view of the apparatus is shown. A gas discharge lamp 30 emits ultraviolet radiation (UV) 20 as a result of being capacitively excited by an external radio frequency voltage (not shown). The radiation passes through a window 100 into an adjacent cell volume 102 which contains molecules 10 of a volatile organic compound. As a result, some percentage of the molecules are ionized by the UV radiation, converting the molecule into positively charged ions and free electrons, according to the equation:

$$M(\text{molecule}) + \text{photon} = M^+(\text{ion}) + e^-(\text{electron}).$$

A pair of electrodes 40, 50 is positioned near the cell volume; one electrode 40 is connected to a high voltage DC source 70, and the other electrode 50 is connected to the input of an amplifier 60. The electric field created by these electrodes forces both the electrons and the ions to migrate toward respective electrodes, where they are collected to produce a very small current flow. The current flow is amplified by the amplifier 60, and the amplifier output signal is displayed or recorded by a connected display/recorder 62.

FIG. 2A shows an isometric exploded view of the gas discharge lamp 30, the detector cell 11, and FIG. 2B shows a further expanded view 12 of the layered construction of the detector cell 11. The gas discharge lamp 30 is preferably made with an outer glass housing 90 and a window 100 made from magnesium fluoride, with krypton gas sealed inside the glass housing 90. Ultraviolet radiation produced by excitation of the Krypton gas readily passes through the window 100.

Adjacent the window 100 is placed a detector cell 11 constructed as a wafer from alumina ceramic material, which has excellent dielectric properties. Detector cell 11 has a plurality of holes 22 forming a hole pattern through the wafer. Each side of the wafer is plated with a metal layer 32, 42, and each metal layer is coated with a thin layer of dielectric material 52, 53. The layers of dielectric material serve to reduce photoemission from the detector cell 11.

Conductors 73, 74 are attached to the metal layers 32, 42. The hole pattern serves as a plurality of open volumes where the ionization of gas and collection of produced charges takes place, as will be explained more fully hereinafter. A high DC voltage is applied to conductor 73, and conductor 74 is connected to the input of amplifier 60. The electrostatic field developed between the metal layers 32 and 42 causes a current flow to the amplifier 60 input, proportional to the ionization of the organic molecules which have collected in the plurality of holes 22.

FIGS. 3A and 3B show an alternative construction of the detector 90, where a third conductive layer 104 is embedded in the detector wafer 11 between the metal layers 32, 42 of FIG. 2B. The purpose of the third conductive layer 104 is to prevent the flow of unwanted current between the electrode conductors 73, 74 over the surface of the cell's dielectric material under conditions when the sample gas has a high moisture content. Conductor 104 is connected to the electrical ground of the circuitry, Conductor 104 is shaped to occupy area outside the cell's holes 22, and it does not affect the electric field inside the holes.

FIG. 4 illustrates an alternative construction wherein the electronic circuitry, including the amplifier 60, an A/D converter (not shown), and other related circuitry can be formed on the same dielectric substrate 22 as the detector cell 11.

FIG. 5 shows an electric circuit which can be used as part of the present invention. A miniature transformer 80 has a secondary winding 82 which is connected to the gas discharge tube's excitation electrodes 83 which, for example, may be plated against the outer surface of the glass lamp 30. A secondary winding tap 84 is connected via a diode 85 to provide a rectified DC voltage Vpol which can be used as the voltage applied between electrodes 40, 50 (FIG. 1). The electric circuit requires a +5V input power supply and conventional filter and feedback circuits, and may be miniaturized for construction.

Figure 6:
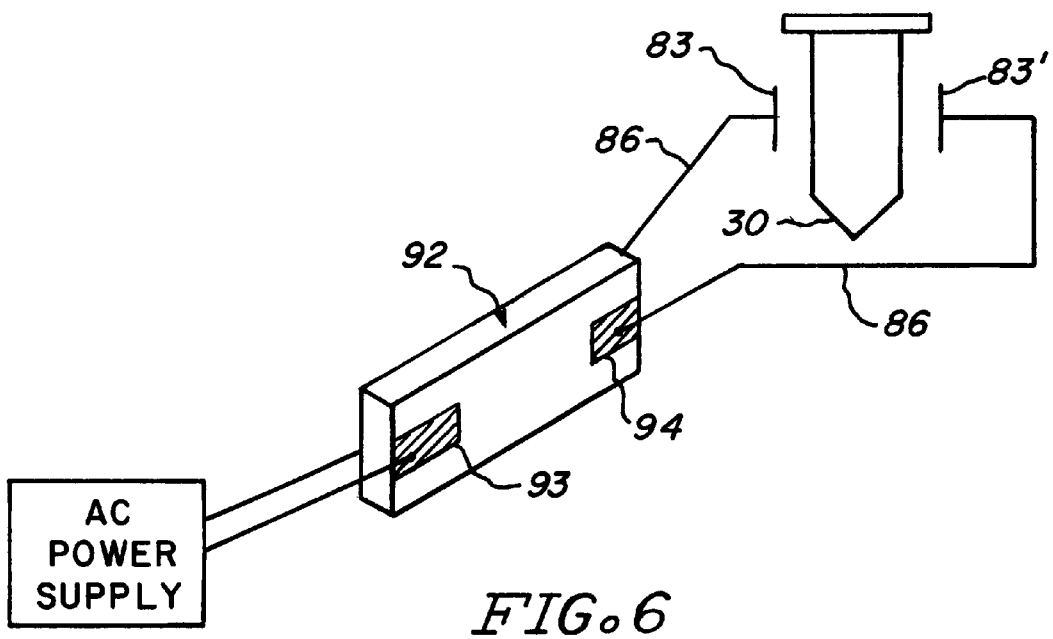
FIG. 6 shows an alternative form of electronic circuit driver.

FIG. 6 shows an alternative circuit design, utilizing a piezoelectric transformer. An AC voltage is applied to the input 93 of this transformer, causing vibration which causes generation of an output voltage to terminals 94. The output voltage is applied to the electrodes 83 which are placed about the surface of glass discharge lamp 30.

Figure 7:
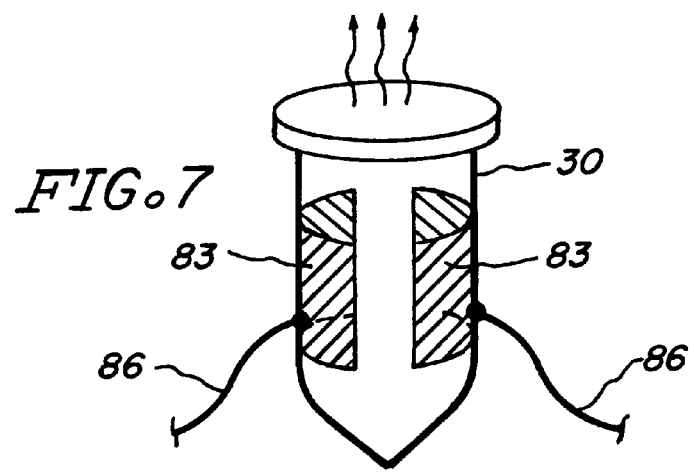
FIG. 7 shows excitation electrodes formed on the outer glass surface of the gas discharge cell.

FIG. 7 shows the gas discharge lamp 30 wherein the excitation electrodes 83 are preferably applied directly to the surface of the lamp by a metal sputtering process. Conductors 86 can be attached to the electrodes 83 with conductive epoxy.

Figure 8:
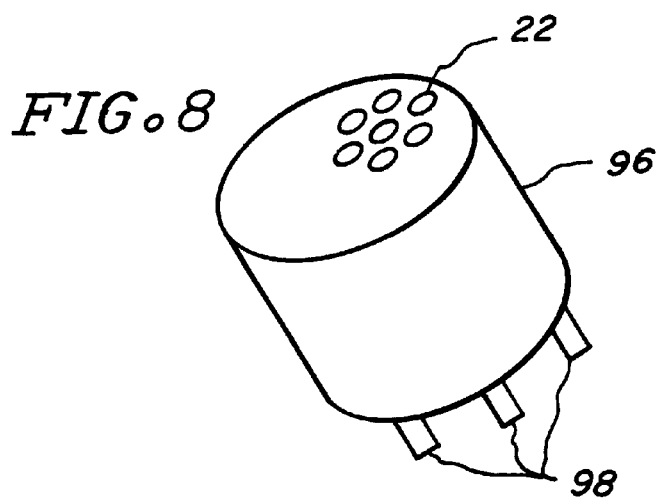
FIG. 8 shows the exterior view of the sensor after assembly of all components.

FIG. 8 shows an exterior view of the invention after all components have been assembled, and are inserted inside a standard plastic housing 96. The hole pattern 22 is exposed at one end of the housing 96 and plug-in connector pins 98 project from the other end of the housing. A typical size for the assembly, including the housing 96 and connector pins 98, is about 20 millimeters (mm), with an outside diameter of about 20 mm. The dimensions of the sensor and the pin layout of its connectors are the same as available on industry-standard electrochemical sensors. Therefore, the sensor is mechanically compatible with a majority of commercial portable gas analyzers (based on electrochemical types of sensors) and can be implemented in those gas analyzers without redesigning them.

Figure 9:
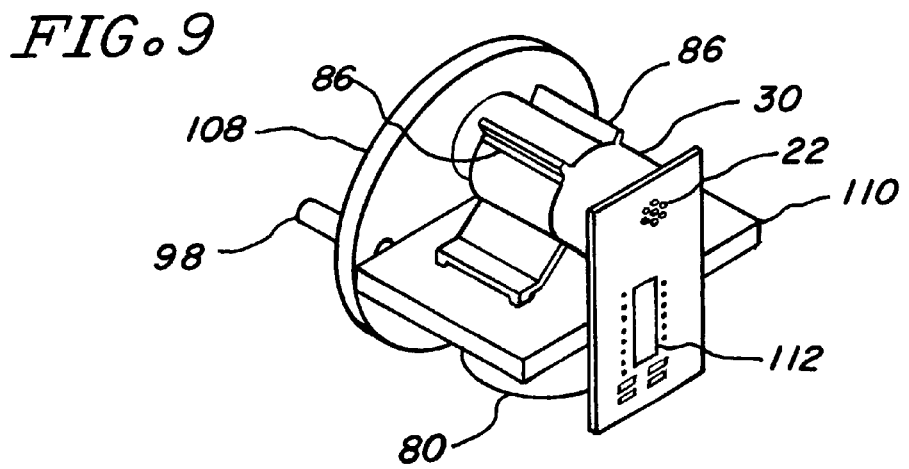
FIG. 9 shows the assembly of FIG. 8 with the outer cover removed.

FIG. 9 shows the assembly without the outer housing 96. The assembly comprises a base 108 through which the connector pins 98 project. The connector pins 98 are suitably connected to a printed circuit board 110 which is attached to the base 108. The electrical transformer 80 (see FIG. 5) is attached to the printed circuit board 110, as are the conductors 86 which lead to the excitation electrodes 83. The detector hole pattern 22 is placed adjacent the window in the gas discharge lamp 30, and a further electronic circuit board carries the electronics associated with the detector.

In operation, the detector cell is placed in an ambient gas location, where the hole pattern 22 is exposed to receive samples of the gas under test. As samples of this gas migrate into the holes of the pattern 22, a certain percentage of the molecules will become ionized, and the ions will be collected by the electrodes as a current. The current is fed into an amplifier and associated circuitry, to produce a signal representative of the measured gas concentration, and the signal may be displayed or recorded as needed.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. A sensor for detecting small concentrations of volatile organic compounds in ambient air, comprising:
   a. a source of ultra-violet radiation confined in a closed housing having a transparent window;
   b. a detector cell positioned adjacent said window, said detector cell having a disk-shaped dielectric body with a pattern of holes therethrough, said holes being open to said ambient air and said volatile organic compounds; each of said holes further comprising an ionization chamber having a depth limited by the thickness of said disk-shaped body; metallic layers directly deposited on opposite outside surfaces of said disk-shaped body; and a dielectric coating over each of said metallic layers;
   c. means for applying a voltage difference to said metallic layers across said dielectric body, thereby to create an electric field across said body; and thereby to create an ion collection field in each of said ionization chambers; and
   d. conductors attached to said metallic layers and connected to an amplifier.

2. The apparatus of claim 1, wherein said source of ultra-violet radiation further comprises a gas discharge lamp containing an inert gas, and means for exciting said gas with radio frequency voltages capacitively applied adjacent said lamp.

3. The apparatus of claim 2, wherein said means for exciting said gas further comprises metal layers directly deposited on the exterior surfaces of said lamp, and a radio frequency voltage applied to said metal layers.

4. The apparatus of claim 3, wherein said inert gas is krypton.

5. The apparatus of claim 3, wherein said dielectric body further comprises a wafer made from alumina ceramic material.

6. The apparatus of claim 5, wherein said lamp further comprises a glass enclosure, and said window further comprises a magnesium fluoride construction.

7. The apparatus of claim 2, wherein said means for exciting said gas further comprises a radio frequency generator having an autotransformer for generating the radio frequency voltage.

8. The apparatus of claim 2, wherein said means for exciting said gas further comprise a piezoelectric generator for generating the radio frequency voltage.

9. The apparatus of claim 1, wherein said detector cell further comprises an intermediate conductive layer in said disk-shaped body, between said outside metallic layers.

10. A sensor for detecting gases which are ionizable by radiation, comprising:
   a. a closed source of radiation having a window for permitting radiation to pass into the exterior;
   b. a detector cell on the exterior of said source and adjacent to said window, said detector cell further comprising a ceramic disk of a predetermined thickness and having a plurality of openings therethrough to opposite surfaces of said disk, and having a metallic layer deposited on each of said opposite surfaces, and having a dielectric layer overlaying each of said of said metallic layers; each of said metallic layer and said dielectric layer respectively having openings in alignment with said plurality of ceramic disk openings; said plurality of openings each further comprising an ionization chamber having a depth equal to the thickness of said ceramic disk; and c. a voltage source connected across said metallic layers for creating and electric field therebetween, and an amplifier connected to receive and amplify current flow created by said electric field.

11. The apparatus of claim 10 wherein said source of radiation further comprises a gas discharge device filled with an inert gas which is excitable by a radio frequency voltage, and a source of radio frequency village applied adjacent said de ice to excite said inert gas, thereby creating photons emitted boy said device.

12. The apparatus of claim 11 wherein said detector cell further comprises a wafer-shaped dielectric material having a pattern of holes therethrough, said hole pattern positioned to receive photons emitted by said device.

13. The apparatus of claim 12, wherein said wafer-shaped dielectric material further comprises an alumina ceramic material.

14. The apparatus of claim 13, wherein said inert gas is krypton.

15. The apparatus of claim 14, further comprising a further intermediate metallic layer in said wafer-shaped ceramic material, said intermediate layer being between said outer metallic layers and having a connection to electrical ground potential.

16. The apparatus of claim 14, further comprising a display device connected to said amplifier, said display device having means for providing a visual display of the current detected and amplified by said amplifier.

17. A sensor for detecting volatile organic compounds in ambient air, comprising:

a. a gas discharge device containing a gas which is excitable to produce photons in a radio frequency field; said discharge device being formed of glass and having an exterior surface at least partially transparent to said photons;

b. a source of radio frequency and a pair of metallic areas on the exterior surface of said gas discharge device, said source of radio frequency connected to said pair of metallic areas to provide radio frequency excitation to said gas;

c. a gas detection cell placed adjacent said gas discharge device, said cell being placed to collect ions of volatile organic compounds in ambient air; said cell being formed of a ceramic disk material having a predetermined thickness, said material having a plurality of openings therethrough to opposite surfaces of said ceramic disk material, each of said plurality of openings further comprising an ionization chamber having a length equal to said disk predetermined thickness; each of said opposite surfaces of said ceramic disk material having a metallic layer coated thereon, and said metallic layers having a dielectric overlayer; said respective metallic layers and said dielectric overlayers having a plurality of opening in respective alignment with each of said plurality of ceramic disk openings;

d. a voltage source connected to said metallic layers to develop an electric field therebetween, and an amplifier connected to said metallic layers to amplify any current developed by said electric field;

whereby photons from said gas discharge device may ionize molecules of volatile organic compounds in said cell, to form ions and free electrons, and said electric field may attract said ions and free electrons to form a current, and said amplifier may amplify said current.

18. The apparatus of claim 17, further comprising a visual display device connected to said amplifier to produce a visual display of the magnitude of the current amplified by said amplifier.

\* \* \* \* \*